United States Patent
Shimura et al.

[11] Patent Number: 5,851,192
[45] Date of Patent: Dec. 22, 1998

[54] CONNECTING STRUCTURE OF THE GUIDE WIRE USED FOR MEDICAL TREATMENT

[75] Inventors: Seiji Shimura, Komaki; Tomihisa Kato, Anjo, both of Japan

[73] Assignee: Asahi Intecc Co., Ltd., Seto, Japan

[21] Appl. No.: 881,645

[22] Filed: Jun. 24, 1997

[51] Int. Cl.⁶ .................................................. A61M 25/00
[52] U.S. Cl. ........................ 600/585; 604/281; 128/772
[58] Field of Search ............................ 600/585; 604/281, 604/280; 128/772

[56] References Cited

U.S. PATENT DOCUMENTS

| | | | |
|---|---|---|---|
| 5,511,559 | 4/1996 | Vance | 128/772 |
| 5,542,434 | 8/1996 | Imran et al. | 604/281 X |
| 5,697,380 | 12/1997 | Quiachon et al. | 604/281 X |

FOREIGN PATENT DOCUMENTS

| | | |
|---|---|---|
| 367472 | 5/1990 | European Pat. Off. |
| 566523 | 10/1993 | European Pat. Off. |
| 9716113 | 5/1997 | WIPO |

*Primary Examiner*—John D. Yasko
*Attorney, Agent, or Firm*—Donald S. Dowden; Cooper & Dunham LLP

[57] ABSTRACT

A connecting structure of the guide wire used for medical treatment herein consisting of a corrugated tube attached to a main guide wire or an extension wire and a straight bar part formed at the end of said extension wire of said main guide wire wherein said straight bar part is inserted into said corrugated tube to fix elastic deformation resistance produced by both of said corrugated tube and said straight bar part. Said connecting structure of the guide wire can be easily and precisely formed and is not disconnected by the force produced in use but can be disconnected when changed.

5 Claims, 3 Drawing Sheets

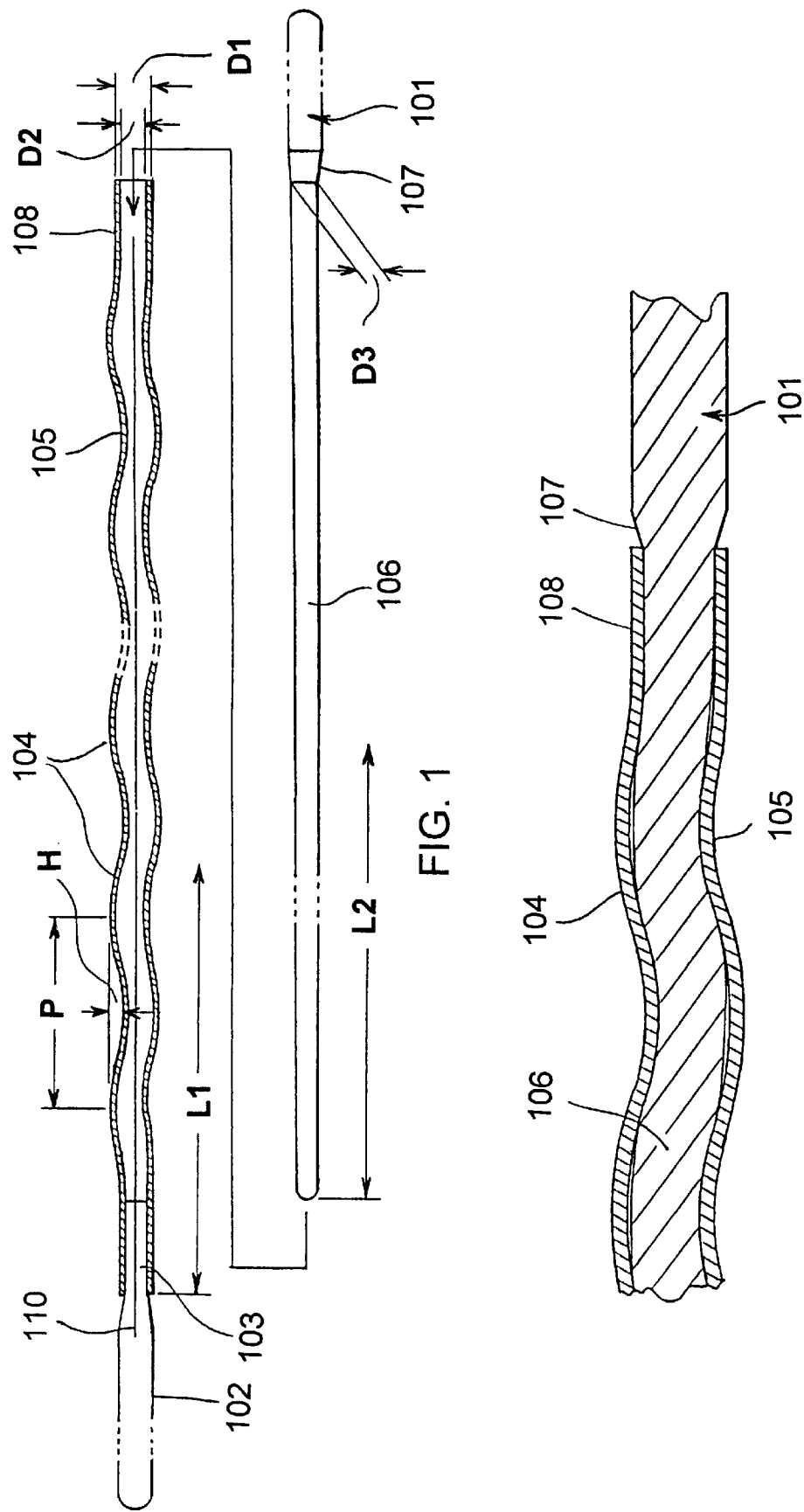

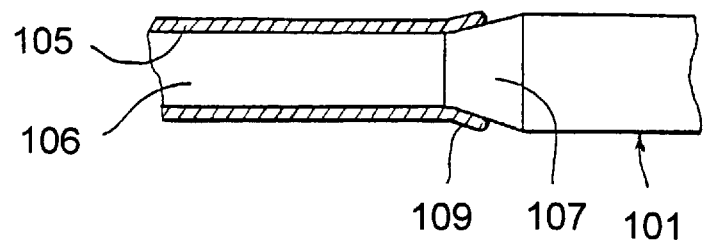
FIG. 3
FIG. 4a
PRIOR ART
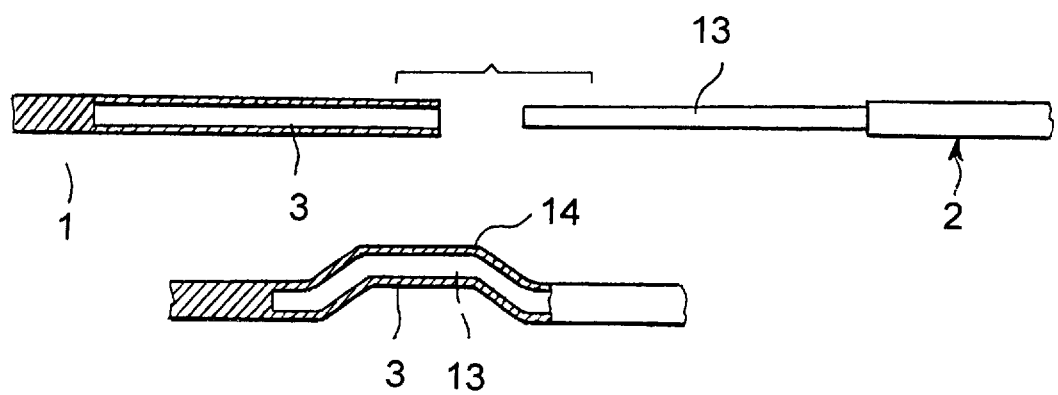
FIG. 4b
PRIOR ART

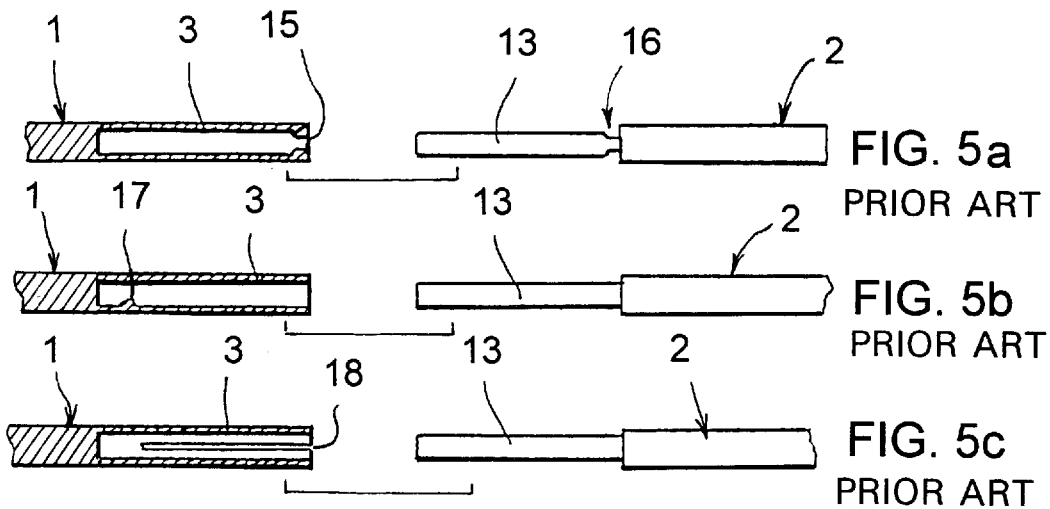
FIG. 5a PRIOR ART
FIG. 5b PRIOR ART
FIG. 5c PRIOR ART
FIG. 6a PRIOR ART
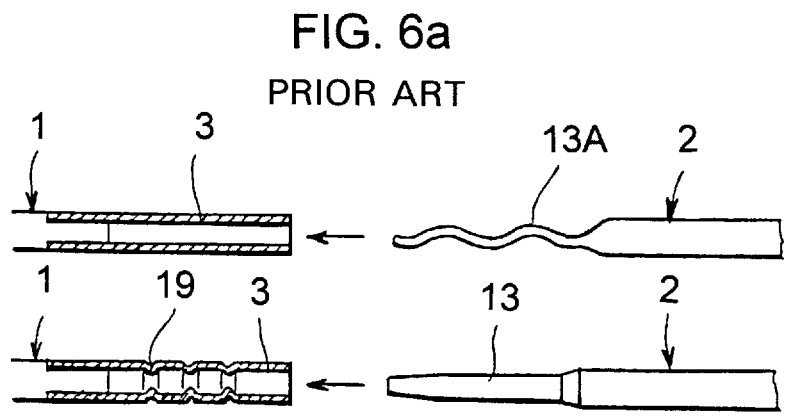
FIG. 6b PRIOR ART

CONNECTING STRUCTURE OF THE GUIDE WIRE USED FOR MEDICAL TREATMENT

FIELD OF THE INVENTION

The present invention relates to a connecting structure of the guide wire used for medical treatment. More particularly, the present invention relates to a connecting structure of the guide wire used for medical treatment consisting of a corrugated tube attached to a main guide wire or an extension wire and a straight bar part formed at the end of said extension wire of said main guide wire wherein said straight bar part is inserted into said corrugated tube to fix elastic deformation resistance produced by both of said corrugated tube and said straight bar part.

DESCRIPTION OF THE PRIOR ART

In medical treatment, a guide wire consisting of a very small flexible wire is used to insert a catheter consisting of a very small flexible tube into the blood vessel. Said catheter may be used for angiography, the treatment of angiostenosis, and the like, and said guide wire is previously inserted into the blood vessel and then said catheter is inserted into the blood vessel along said guide wire.

In a case of the balloon catheter used for the treatment of angiostenosis, the plural number of balloon catheters having various expanding diameters are prepared and said balloon catheters are inserted into the blood vessel in order from the balloon catheter having a smaller expanding diameter.

In the case of the catheter used for the treatment of angiostenosis, at least three kinds of catheters, for the left coronaria, the right coronaria, and the pigtail catheter, should be prepared and said catheters are inserted into the blood vessel one by one.

As above described, in a case where the plural number of catheters are inserted into the blood vessel one by one, the guide wire should be repeatedly inserted and extracted into/from the blood vessel(s) to insert each catheter. Nevertheless, said repeated insertion and extraction of the guide wire give the patient a big stress, increase the number of treatment procedures and extend the treatment time. Further, it is feared that the blood vessel is injured by said repeated insertion and extraction of the guide wire.

To solve this problem, a guide wire consisting of a main guide wire and an extension wire has been provided. Said guide wire is inserted into the blood vessels such that said main guide wire is inside of the body and said extension wire is outside of the body. Accordingly, in this type of guide wire, when the catheter is changed, only said extension wire outside of the body is necessary to change keeping said main guide wire in the body.

Hitherto, the connecting structures between said main guide wire and said extension guide wire have been provided in such as Tokko Hei 7-10280, U.S. Pat. No. 4,922,923, U.S. Ser. No. 137963 and Tokkai Hei 5-92044. For instance, as shown in FIG. 4a and b, a tube (3) is formed at the end of said main guide wire (1) and a straight bar part (13) having a smaller diameter than said extension wire (2) is formed at the end of said extension wire (2) to insert said straight bar part (13) of said extension wire (2) into said tube (3) of said main guide wire (1) and then said tube (3) is bent with said straight bar part (13) to form a crank part (14) to fix said straight bar part (13) in said tube (3) as shown in FIG. 4b.

Further, for instance, as shown in FIG. 5a, clicks (15) are formed at the end of said tube (3) of said main guide wire (1) to engage said clicks (15) with ditches (16) formed at the root of said straight bar part (13), still further, as shown in FIG. 5b, a projection (17) is formed inside of said tube (3) of said main guide wire (1) to press said projection (17) to said straight bar part (13), still further, as shown in FIG. 5c, a slit (18) is formed along said tube (3) of said main guide wire (1) to calk said tube (3) to said straight bar part (13) of said extension wire (2).

Still further, as shown in FIG. 6a, a corrugated bar part (13A) is formed at the end of said extension wire (2) and when said corrugated bar part (13A) is inserted into said straight tube (3) of said main guide wire (1), said corrugated bar part (13A) is fixed in said straight tube (3) by elastic deformation resistance and still further, as shown in FIG. 5b, calking parts (19) are formed in said tube (3) of said main guide wire (1) to fix said straight bar part (13) of said extension wire (2).

The connecting structure shown in FIG. 4 has a crank part (14) and said crank part (14) is difficult to form and further said crank part (14) interfere with smooth insertion and extraction of the guide wire into/from the blood vessel and also interfere with pulling said extension wire (2) from said main guide wire (1).

The connecting structure shown in FIG. 5 has a loose connection between said main guide wire (1) and said extension wire (2) and it is feared to disconnect said extension wire (2) from said main guide wire (1) during treatment, and further, small click (15), small projection (17) and small slit (18) are difficult to form in said tube (3).

In the connecting structure shown in FIG. 6a, since said corrugated bar part (13A) has a small diameter such as about 0.35 mm, to result in a small rigidity of said corrugated bar part (13A), the elastic deformation resistance is small and it is also feared to disconnect said extension wire (2) from said main guide wire (1) during treatment, and further, since said corrugated bar part (13A) is deformed by inserting said corrugated bar part (13A) into said tube (3), said extension wire (2) can not be used repeatedly, and the connecting structure shown in FIG. 6b has small contacting area between said calking parts (19) of said tube (3) and said straight bar part (13), and further, it is difficult to form precisely said small calking parts (19), the disconnection between said main wire and said extension wire is also feared.

SUMMARY OF THE INVENTION

Accordingly, an object of the present invention is to provide a connecting structure of the guide wire which can be easily and precisely formed.

A further object of the present invention is to provide a connecting structure of the guide wire which is not disconnected by the force produced in use but can be disconnected when the extension wire is changed.

A still further object of the present invention is to provide a connecting structure of the guide wire which can be used repeatedly.

Briefly, said objects of the present invention can be attained by a connecting structure of the guide wire used for medical treatment consisting of a corrugated tube attached to a main guide wire or an extension wire and a straight bar part formed at the end of said extension wire of said main guide wire wherein said straight bar part is inserted into said corrugated tube to fix elastic deformation resistance produced by both of said corrugated tube and said straight bar part.

BRIEF DESCRIPTION OF THE DRAWINGS

FIG. 1 and FIG. 2 relate to an embodiment of the present invention.

FIG. 1 shows a side sectional view of a tube and a straight bar part.

FIG. 2 shows a side sectional view of the bar part inserted into said tube.

FIG. 3 shows a side sectional view of another embodiment.

FIG. 4 to FIG. 6 relate to a traditional connecting structure.

FIG. 4a is a side sectional view of an illustration of a tube and a straight bar part in a traditional connecting structure.

FIG. 4b is a side sectional view of a straight bar part inserted into said tube.

FIG. 5a shows a side sectional view of a further illustration of a tube and a straight bar part in a traditional connecting structure.

FIG. 5b shows a side sectional view of a still further illustration of a tube and a straight bar part in a traditional connecting structure.

FIG. 6a shows a side sectional view of a still further illustration of a tube and a straight bar part in a traditional connecting structure.

FIG. 6b shows a side sectional view of a still further illustration of a tube and a straight bar part in a traditional connecting structure.

DETAILED DESCRIPTION

FIG. 1 and FIG. 2 relate to an embodiment of the present invention. Referring now to Figs., a main guide wire (101) consisting of a very thin stainless steel wire and to be inserted into the blood vessel and an extension wire (102) are connected together through a corrugated tube (105). More precisely, said corrugated tube (105) is made of a stainless steel, an alloy such as a titan-nickel alloy and the like and a straight tube part (108) is formed at one end of said corrugated tube (105), and one end (103) of said extension wire (102) having a contracted diameter is inserted into the other end of said corrugated tube (105) and fixed by staking, blazing, and the like and one end of said main guide wire (101).

A straight bar part (106) having a contracted diameter forms at one end of said main guide wire (101) through a tapering part (107) and said straight bar part (106) has a slightly tapering shape and a round top. In this embodiment, said corrugated tube (105) has a length L1=30 mm, an inside diameter D2=0.23 mm, an outside diameter D1=0.34 mm, the height of corrugated shape (104) H=0.12 mm and the pitch of corrugated shape (104) P=5 mm, said straight bar part (106) of said main guide wire (101) has a length L2=17 mm, the diameter of the root D3=0.22 mm, and said main guide wire (101) and said extension wire (102) have a diameter of 0.35 mm respectively, and said corrugated tube (105) has a higher rigidity than said straight bar part (106) of said main guide wire (101) by its tubular rib effect.

Said main guide wire (101) and said extension wire (102) are connected together by inserting said straight bar part (106) of said main guide wire (101) into said corrugated tube (105) of said extension wire (102). When said straight bar part (106) of said main guide wire (101) is inserted into said corrugated tube (105), since said corrugated tube (105) has a higher rigidity than said straight bar part (106) as above described, said straight bar part (106) may be elastically bent along the corrugate profile of said corrugated tube (105) and at the same time, the corrugate profile of said corrugated tube (105) may be elastically deformed and become loose by the elastic deformation resistance of said straight bar part (106) as shown in FIG. 2. As a result, said straight bar part (106) is fixed in said corrugated tube (105) by both of the elastic deformation resistance produced by said straight bar part (106) and the elastic deformation resistance produced by said corrugated tube (105), such that said connecting part between said main guide wire (101) and said extension wire (102) is not disconnected by the force produced by inserting said main guide wire (101) into the blood vessel but disconnected by pulling strongly by hands.

Further, said corrugated tube (105) can be easily wrought into a desired corrugate shape and the abrasion of both of said corrugated tube (105) and said straight bar part (106) by repeated inserting-pulling cycle is very small.

FIG. 3 shows an alteration of the above described embodiment. In this alteration, a tapering part (109) is formed at the end of said corrugated tube (105) corresponding with said tapering part (107) of said main guide wire (101). When said straight bar part (106) is inserted into said corrugated tube (105), said tapering part (107) of said main guide wire (101) fits said tapering part (109) of said corrugated tube (105) to prevent the stress concentration at the root of said straight bar part (106). Further, the end of said corrugated tube (105) may be annealed to soften this part. In a case where a titan-nickel alloy is used as a material for said corrugated tube (105), it is desirable to set the annealing temperature in the range between about 680° to 715° C., and in the case where a stainless steel is used as a material for said corrugated tube (105), it is desirable to set the annealing temperature in the range between about 800° to 900° C. Still further, said corrugated tube (105) may be attached to the main guide wire (101) and said straight bar part (106) may be formed at the end of said extension wire (102).

As above described, the connecting structure of the present invention can be easily formed by inserting said straight bar part (106) into said corrugated tube (105) and fixed such that said connecting structure is not disconnected by the force produced in use but when said connecting structure is pulled strongly by hand, said connecting structure is easily disconnected. Further, since the abrasion of both of said corrugated tube (105) and said straight bar part (106) by repeated inserting-pulling cycle is very small, the guide wire of the present invention can be used repeatedly many times. Still further, since said connecting structure of the present invention has a smooth corrugated shape without an angle, said connecting structure does not injure the blood vessel when the guide wire is inserted into the blood vessel.

We claim:

1. A connecting structure of the guide wire used for medical treatment consisting of a corrugated tube attached to a main guide wire or an extension wire and a straight bar part formed at the end of said extension wire of said main guide wire wherein said straight bar part is inserted into said corrugated tube to fix elastic deformation resistance produced by both of said corrugated tube and said straight bar part.

2. A connecting structure of the guide wire in accordance with claim 1 wherein the rigidity of said corrugated tube is higher than the rigidity of said straight bar part.

3. A connecting structure of the guide wire in accordance with claim 1 wherein a tapering part is formed at the root of said straight bar part.

4. A connecting structure of the guide wire in accordance with claim 3 wherein a tapering part fitting said tapering part of said straight bar part is formed at the end of said corrugated tube.

5. A connecting structure of the guide wire in accordance with claim 1 wherein the end of said corrugated tube is annealed to soften.

* * * * *